United States Patent
Castro et al.

(10) Patent No.: US 6,899,734 B2
(45) Date of Patent: May 31, 2005

(54) MODULAR IMPLANT FOR FUSING ADJACENT BONE STRUCTURE

(75) Inventors: Michael Castro, Seymour, CT (US); Herb Cohen, Shelton, CT (US); David Nichols, Trumbull, CT (US); Scott R. Graham, Richmond, VA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 09/815,504

(22) Filed: Mar. 23, 2001

(65) Prior Publication Data

US 2002/0138142 A1 Sep. 26, 2002

(51) Int. Cl.$^7$ .................................................. A61F 2/44
(52) U.S. Cl. .................................................. 623/17.16
(58) Field of Search .......................... 623/17.11–17.16

(56) References Cited

U.S. PATENT DOCUMENTS

| | | |
|---|---|---|
| 2,677,369 A | 5/1954 | Knowles |
| 3,426,364 A | 2/1969 | Lumb |
| 3,486,505 A | 12/1969 | Morrison |

(Continued)

FOREIGN PATENT DOCUMENTS

| | | |
|---|---|---|
| CA | 2015507 | 1/1991 |
| DE | 25 42 056 | 3/1977 |
| DE | 28 24 678 | 12/1979 |
| DE | 31 13142 A1 | 1/1982 |
| DE | 43 28 690 A1 | 3/1995 |
| EP | 0 077 159 | 4/1983 |
| EP | 0 322 334 B1 | 6/1989 |
| EP | 0 716 840 A2 | 6/1996 |
| EP | 0 796 593 A2 | 9/1997 |
| FR | 736213 | 11/1932 |
| FR | 2295729 | 12/1974 |
| FR | 2681 525 | 3/1993 |
| FR | 2706309 | 12/1994 |
| JP | 57-29348 | 2/1982 |
| JP | 58-78653 | 5/1983 |
| JP | 61-16572 | 1/1986 |
| JP | 61-135652 | 6/1986 |
| JP | 62-29344 | 2/1987 |
| JP | 62-164458 | 7/1987 |
| JP | 1-314560 | 12/1989 |
| JP | 10-314560 | 12/1998 |
| SU | 1484348 A1 | 6/1989 |
| WO | WO 87/07827 | 12/1987 |
| WO | WO 89/12431 | 12/1989 |
| WO | WO 90/00037 | 1/1990 |
| WO | WO 91/06261 | 5/1991 |
| WO | WO 91/16018 | 10/1991 |
| WO | WO 94/17759 | 8/1994 |
| WO | WO 95/22946 | 8/1995 |
| WO | WO 95/32673 | 12/1995 |
| WO | WO 95/35180 | 12/1995 |
| WO | WO 9608205 A1 | 3/1996 |
| WO | WO 96/27321 | 9/1996 |
| WO | WO 96/27339 | 9/1996 |
| WO | WO 99/56675 | 11/1999 |

*Primary Examiner*—Alvin Stewart
(74) *Attorney, Agent, or Firm*—Lerner, David, Littenberg, Krumholz & Mentlik, LLP (57) ABSTRACT

A fusion implant apparatus for facilitating fusion of bone structures includes an implant member for positioning between opposed bone structures having a first ring-like segment and a second ring-like segment which engage one another in an end-to-end manner. Each ring-like segment includes an outer wall which defines an internal cavity for the reception of bone growth inducing substances. Each ring-like segment also includes a plurality of apertures which extend through the outer wall of the ring-like segments in communication with the internal cavity to permit fusion of vertebral bone tissue. The first ring-like segment includes first and second mechanical interfaces. The first mechanical interface is dimensioned to engage a corresponding mechanical interface disposed on the second ring-like segment and the second mechanical interface is dimensioned to mechanically engage an end cap.

29 Claims, 5 Drawing Sheets

U.S. PATENT DOCUMENTS

| | | |
|---|---|---|
| 3,648,691 A | 3/1972 | Lumb et al. |
| 3,719,186 A | 3/1973 | Merig, Jr. |
| 3,848,601 A | 11/1974 | Ma et al. |
| 3,867,728 A | 2/1975 | Stubstad et al. |
| 3,867,932 A | 2/1975 | Huene |
| 3,905,047 A | 9/1975 | Long |
| 3,916,907 A | 11/1975 | Peterson |
| 4,059,115 A | 11/1977 | Jumashev et al. |
| 4,177,524 A | 12/1979 | Grell et al. |
| 4,309,777 A | 1/1982 | Patil |
| 4,328,593 A | 5/1982 | Sutter et al. |
| 4,343,321 A | 8/1982 | Caranicas |
| 4,401,112 A | 8/1983 | Rezaian |
| 4,479,491 A | 10/1984 | Martin |
| 4,484,570 A | 11/1984 | Sutter et al. |
| 4,501,269 A | 2/1985 | Bagby |
| 4,537,185 A | 8/1985 | Stednitz |
| 4,545,374 A | 10/1985 | Jacobson |
| 4,553,273 A | 11/1985 | Wu |
| 4,573,448 A | 3/1986 | Kambin |
| 4,599,084 A | 7/1986 | Nashef |
| 4,636,217 A | 1/1987 | Ogilvie et al. |
| 4,657,550 A | 4/1987 | Daher |
| 4,677,972 A | 7/1987 | Tornier |
| 4,714,469 A | 12/1987 | Kenna |
| 4,743,256 A | 5/1988 | Brantigan |
| 4,772,287 A | 9/1988 | Ray et al. |
| 4,790,303 A | 12/1988 | Steffee |
| 4,820,305 A | 4/1989 | Harms et al. |
| 4,834,757 A | 5/1989 | Brantigan |
| 4,877,020 A | 10/1989 | Vich |
| 4,878,915 A | 11/1989 | Brantigan |
| 4,904,260 A | 2/1990 | Ray et al. |
| 4,904,261 A | 2/1990 | Dove et al. |
| 4,927,421 A | 5/1990 | Goble et al. |
| 4,932,975 A | 6/1990 | Main et al. |
| 4,936,848 A | 6/1990 | Bagby |
| 4,936,851 A | 6/1990 | Fox et al. |
| 4,961,740 A | 10/1990 | Ray et al. |
| 4,978,350 A | 12/1990 | Wagenknecht |
| 5,011,484 A | 4/1991 | Breard |
| 5,015,247 A | 5/1991 | Michelson |
| 5,015,255 A | 5/1991 | Kuslich |
| 5,055,104 A | 10/1991 | Ray |
| 5,059,193 A | 10/1991 | Kuslich |
| 5,062,845 A | 11/1991 | Kuslich et al. |
| 5,092,866 A | 3/1992 | Breard et al. |
| 5,180,381 A | 1/1993 | Aust et al. |
| 5,192,327 A | 3/1993 | Brantigan |
| 5,258,031 A | 11/1993 | Salib et al. |
| 5,263,953 A | 11/1993 | Bagby |
| 5,300,076 A | 4/1994 | Leriche |
| 5,313,962 A | 5/1994 | Obenchain |
| 5,358,511 A | 10/1994 | Gatturna et al. |
| 5,387,213 A | 2/1995 | Breard et al. |
| 5,395,317 A | 3/1995 | Kambin |
| 5,395,372 A | 3/1995 | Holt et al. |
| 5,400,805 A | 3/1995 | Warren |
| 5,415,661 A | 5/1995 | Holmes |
| 5,423,816 A | 6/1995 | Lin |
| 5,423,817 A | 6/1995 | Lin |
| 5,425,772 A | 6/1995 | Brantigan |
| 5,431,658 A | 7/1995 | Moskovich |
| 5,439,464 A | 8/1995 | Shapiro |
| 5,443,514 A | 8/1995 | Steffee |
| 5,454,811 A | 10/1995 | Huebner |
| 5,458,638 A | 10/1995 | Kuslich et al. |
| 5,458,641 A | 10/1995 | Ramirez Jimenez |
| 5,470,334 A | 11/1995 | Ross et al. |
| 5,480,403 A | 1/1996 | Lee et al. |
| 5,484,437 A | 1/1996 | Michelson |
| 5,489,307 A | 2/1996 | Kuslich et al. |
| 5,489,308 A | 2/1996 | Kuslich et al. |
| 5,496,318 A | 3/1996 | Howland et al. |
| 5,505,732 A | 4/1996 | Michelson |
| 5,522,899 A | 6/1996 | Michelson |
| 5,534,031 A | 7/1996 | Matsuzaki et al. |
| 5,549,679 A | 8/1996 | Kuslich |
| 5,554,191 A | 9/1996 | Lahille et al. |
| D374,283 S | 10/1996 | Michelson |
| 5,562,736 A | 10/1996 | Ray et al. |
| 5,571,109 A | 11/1996 | Bertagnoli |
| 5,571,189 A | 11/1996 | Kuslich |
| 5,571,192 A * | 11/1996 | Schonhoffer .............. 623/17.11 |
| 5,591,235 A | 1/1997 | Kuslich |
| 5,593,409 A | 1/1997 | Michelson |
| 5,609,635 A | 3/1997 | Michelson |
| 5,609,636 A | 3/1997 | Kohrs et al. |
| 5,702,455 A | 12/1997 | Saggar |
| 5,741,253 A | 4/1998 | Michelson |
| D397,436 S | 8/1998 | Michelson |
| 5,797,909 A | 8/1998 | Michelson |
| 6,015,436 A * | 1/2000 | Schonhoffer .............. 623/17.16 |
| 6,558,423 B1 * | 5/2003 | Michelson ............... 623/17.11 |

\* cited by examiner

MODULAR IMPLANT FOR FUSING ADJACENT BONE STRUCTURE

BACKGROUND

The present disclosure generally relates to a surgical apparatus for fusing adjacent bone structures, and, more particularly, to a segmented and/or modular apparatus and method for fusing adjacent vertebrae.

TECHNICAL FIELD

The fusion of adjacent bone structures is commonly performed to provide for long-term replacement to compensate for vertebral subluxation typically caused by severe trauma to the spine, degenerative or deteriorated bone disorders, e.g., osteoporosis, abnormal curvature of the spine (scoliosis or kyphosis) and/or weak or unstable spine conditions typically caused by infections or tumors. In addition, an intervertebral disc, which is a ligamentous cushion disposed between adjacent vertebrae, may also undergo deterioration or degeneration as a result of injury, disease, tumor or other disorders. The disk shrinks or flattens leading to mechanical instability and painful disc translocations, commonly referred to as a "slipped disc" or "herniated disc".

Conventional procedures for disc surgery include partial or total excision of the injured disc portion, e.g., discectomy, and replacement of the excised disc with biologically acceptable plugs or bone wedges. The plugs are driven between adjacent vertebrae to maintain normal intervertebral spacing and to achieve, over a period of time, bony ingrowth or "fusion" with the plug and opposed vertebrae.

Alternatively, a metallic fusion cage may be inserted within a tapped bore or channel formed in the intervertebral space thereby stabilizing the vertebrae and maintaining a pre-defined intervertebral space. A pair of fusion cages may also be implanted within the intervertebral space. After a period of time, the soft cancellous bone of the surrounding vertebral bone structures infiltrates the cage through a series of apertures in the cage wall and unites with bone growth inducing substances disposed within an internal cavity of the cage wall to eventually form a solid fusion of the adjacent vertebrae.

SUMMARY

The present disclosure relates to a fusion implant apparatus for facilitating fusion of adjacent bone structures. The fusion apparatus includes a modular implant member for positioning between adjacent opposed bone structures and having a plurality of ring-like segments which engage one another in an end-to-end or stack-like manner. Each ring-like segment includes an outer wall which defines an internal cavity for the reception of bone growth inducing substances and includes a plurality of apertures which extend through the outer wall of the ring-like segments in communication with the internal cavity to permit fusion of vertebral bone tissue. Preferably, at least one ring-like segment includes first and second mechanical interfaces, the first mechanical interface being dimensioned to engage a corresponding mechanical interface disposed on another ring-like segment and the second mechanical interface being dimensioned to mechanically engage an end cap. At least one ring segment preferably incorporates a C-shaped or split ring configuration with semi-resilient characteristics to facilitate engagement with another ring-like segment.

The end cap preferably includes a plurality of detents or spike-like protrusions which project outwardly therefrom and which are designed to anchor the fusion cage to the underside of the vertebral bodies. The end cap may also include one or more flanges, retaining sleeves, locking pins, or other mechanically interfacing mechanism for securing the end cap to the body of the implant member. In one embodiment, the end cap has a C-shaped or split ring configuration to facilitate mounting the end cap to the implant member.

DETAILED DESCRIPTION

Figure 1:
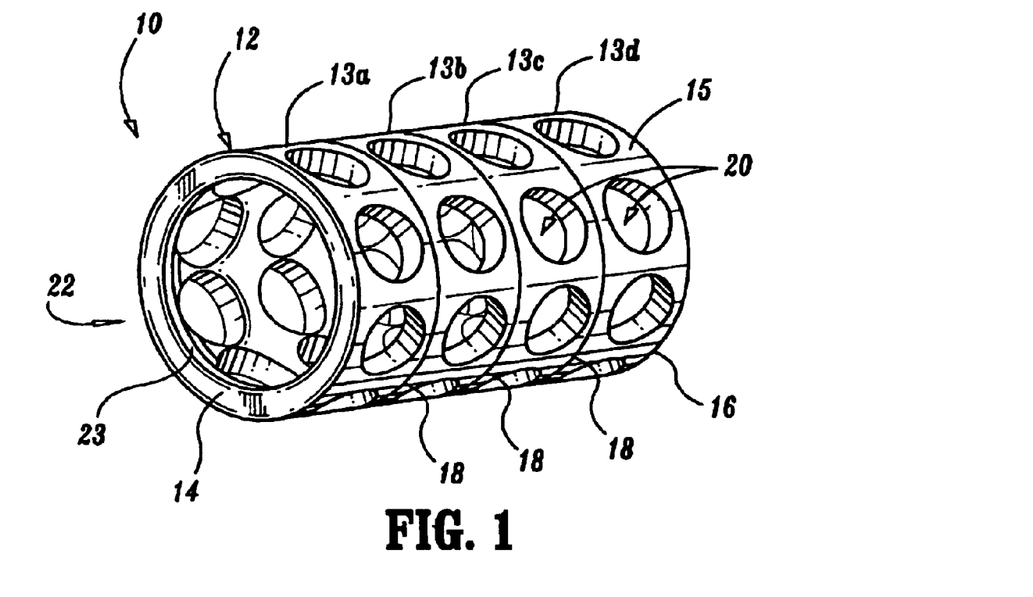
FIG. 1 is a perspective view of a modular fusion cage according to the present disclosure.

Referring now to the drawings in which like reference numerals identify similar or identical elements throughout the several views, FIG. 1 illustrates one embodiment of a modular fusion cage implant 10 according to the present disclosure. Fusion implant 10 includes a generally elongated body 12 having a first end 14, a second end 16 and an end cap 40 (FIGS. 3A–3C) which is mountable to the body 12.

Cage 10 is preferably fabricated from a suitable biocompatible rigid material such as titanium and/or alloys of titanium, stainless steel, ceramic materials or rigid polymeric materials. Moreover, it is envisioned that cage 10 is sufficient in strength to at least partially replace the supporting function of an intervertebral disc, i.e., to maintain adjacent vertebrae in desired spaced relation, during healing and fusion.

Figure 5A:
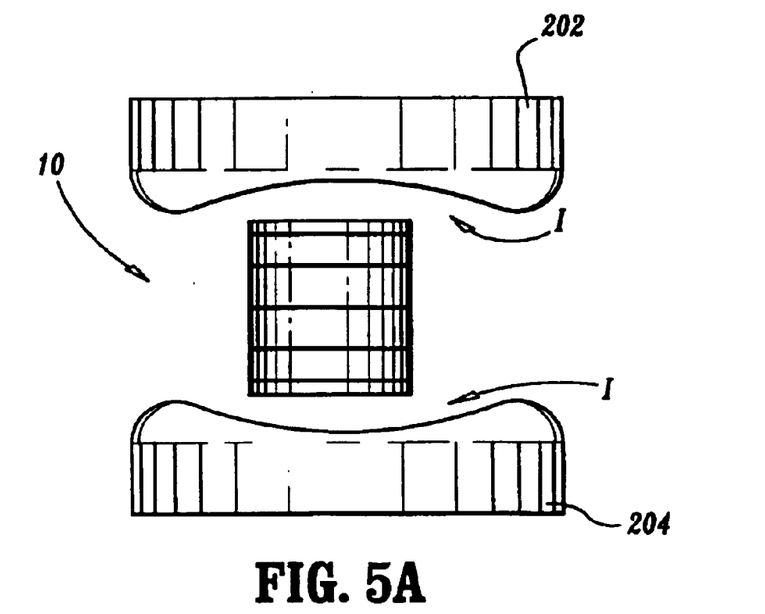
FIG. 5A is a schematic, lateral view showing the placement of the fusion cage of FIG. 1 between two adjacent vertebrae.

As best shown in FIG. 1, the body 12 of cage 10 includes an outer wall 15 which encloses an inner cavity 22 defined within the interior of the cage body 12. Inner cavity 22 accommodates bone growth substances which induce the soft cancellous bone surrounding the vertebrae to grow inwardly towards the contact surfaces of the fusion cage 10 to stabilize the cage 10 between two adjacent vertebrae 202, 204 (See FIGS. 5A and 5B). It is envisioned that outer wall 15 can be designed in a variety of different shapes depending upon a specific purpose, e.g., oval-shaped, kidney-shaped, etc. It is also envisioned that the surface of outer wall 15 may be coated with a variety of different materials which facilitate insertion of the cage 10 and enhance retention of the cage 10 between opposing vertebrae 202, 204.

As best shown in FIG. 1, a plurality of apertures 20 extend through outer wall 15 of cage body 12 and preferably promote immediate bone to bone contact between the vertebral bodies 202, 204 and the bone inducing substances packed within the internal cavity 22 of the cage body 12. Such arrangement of apertures 20 is disclosed in commonly assigned U.S. Pat. Nos. 4,961,740 and 5,026,373, the contents of which are hereby incorporated by reference. Apertures 20 are preferably substantially the same in dimension although it is envisioned that the dimensions of the apertures 20 may vary to provide for more or less bone-to-bone contact depending upon a particular purpose.

Preferably, apertures 20 are oriented such that when the cage 10 is inserted between the upper and lower vertebral bone structures 202, 204, the apertures 20 encourage bony ingrowth through cage body 12 from the vertebral bone structures 202, 204.

As shown in FIG. 1, the body 12 of cage 10 includes seam or grooves 18 which encircle the outer periphery of body 12. Grooves 18 segment the body 12 into discrete ring-like segments, e.g., 13a, 13b, 13c and 13d. Preferably, the grooves 18 act as cutting guides as well as measurement guides in determining the desired length of the fusion cage 10 needed. It is envisioned that the height of each ring-like segment, e.g., 13a, and therefore, the distance between each corresponding groove 18, may be varied depending upon a particular purpose.

Figure 2:
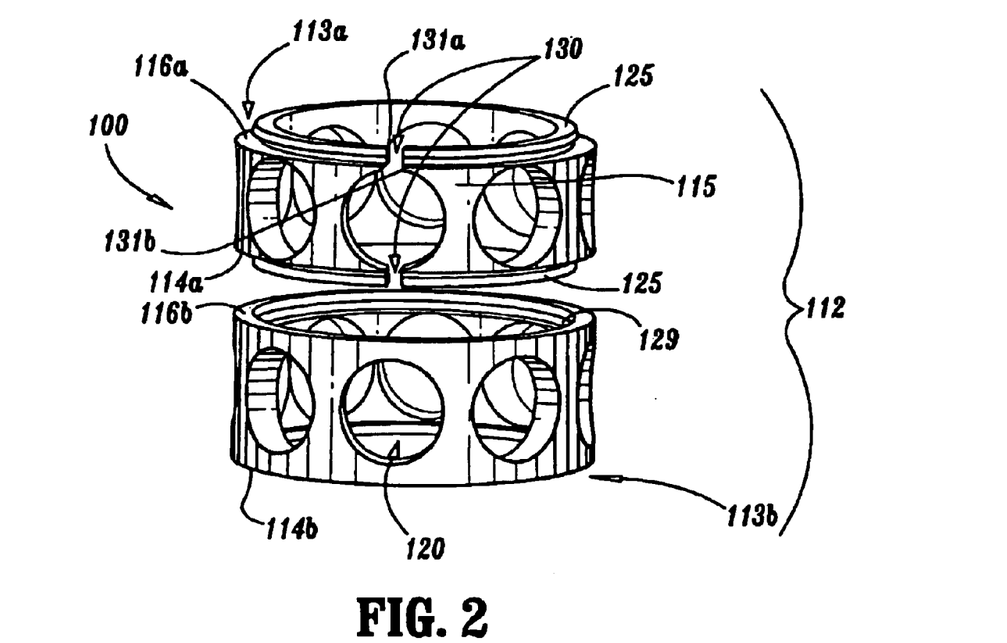
FIG. 2 is a side view with parts separated of an alternate embodiment of the modular fusion cage of the present disclosure.

One embodiment of a fusion cage 100 according to the present disclosure is illustrated in FIG. 2 and includes a plurality of ring-like segments 113a and 113b which mechanically engage one another in an end-to-end or stack-like manner to form elongated tube body 112. Each ring segment, 113a, 113b, includes a plurality of apertures 120 located therethrough which are appropriately sized to promote immediate bone to bone contact between the vertebral bodies 202, 204 (FIG. 5A) and the bone inducing substances as described above. The first end of ring-like segment 113a, e.g., end 114a, preferably includes a mechanical interface, e.g., flange 125, which is dimensioned to mechanically engage a corresponding annular recess or lip 129 disposed within the opposed end 116b of ring-like segment 113b. The ring segments 113a, 113b may be designed with other types of mechanically engaging interfaces depending upon a particular purpose, e.g., interlocking wedges, locking pins, etc.

As can be appreciated, groove 18 is formed as a result of the union of the two ring-like segments 113a, 113b. The grooves 18 may project from body 12 and include sharp edges which eliminate the need for any internal rings in the sizing device. It is envisioned that the grooves will also promote subsidence into the vertebral bodies 202, 204.

Figure 3A:
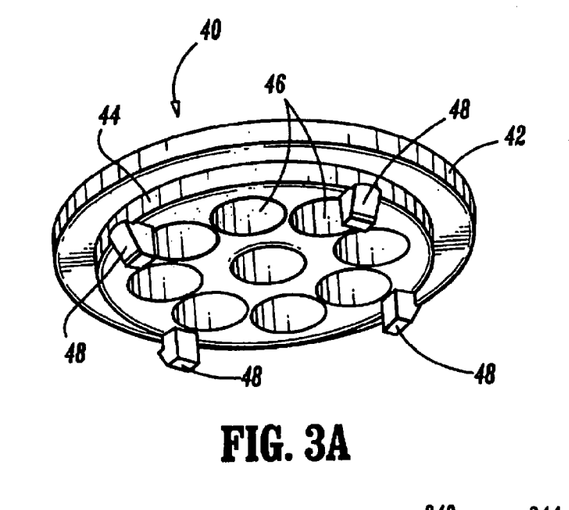
FIG. 3A is a bottom, perspective view of one embodiment of the end cap according to the present disclosure showing a plurality of locking pins projecting from an inner diameter of the end cap.

End 116a of ring segment 113a includes a flange 125 which is designed to engage a third ring segment (not shown) to further the length of elongate body 112 depending upon a particular purpose or, alternatively, the flange 125 may engage an end cap 40 in a manner described below with respect to FIGS. 3A–3C. It is envisioned that the end 114b of ring segment 113b may also include a mechanical interface (not shown) designed to engage another ring segment (not shown) or, alternatively, a second end cap 40 if needed.

As can be appreciated by the present disclosure, no screws are required to assemble the various components of the cage 100, i.e., the ring segments 113a, 113b, etc. and the end caps 40, 140, 240, 340, 440 and 540 as described below prior to and/or during implantation. Moreover, the size, number and shape (e.g., oval shape, kidney-shape, etc.) of the of ring-like segments 113a, 113b may vary enabling the surgeon to quickly and easily customize each fusion cage 100 according to the pre-defined intervertebral space "I" between a patient's opposing vertebrae 202, 204.

As best shown in FIG. 2, ring segment 113a may also be designed in a C-shaped or split-ring configuration to facilitate engagement with ring segment 113b. More particularly, ring segment 113a includes a pair of opposing edges 131a, 131b, respectively, which define an open slit 130 in the outer wall 115 thereof which enables a surgeon to radially compress ring segment 113a inwardly enabling facile mechanical engagement of flange 125 with the lip 129 of ring segment 113b. Once flange 125 and lip 129 are properly aligned or seated, i.e., engaged, the surgeon simply reduces inward compressive pressure to interlock the two ring segments 113a and 113b together. The surgeon simply compresses ring 113a again to disengage the two ring segments 113a, 113b if needed. As can be appreciated, a surgeon can quickly and easily change the size and shape of the cage 100 as needed to ensure proper positioning within the intervertebral space "I" between opposing vertebrae 202, 204.

As stated above, it is also envisioned that cage 10, 100 can be dimensioned such that cage 10, 100 is generally symmetrical, i.e., end-to-end symmetry, which permits insertion of the cage 10 from either end 14, 16.

FIGS. 3A–4C disclose various configurations of the end cap 40 which mounts to the elongated body 12, 112. As can be appreciated, the end cap 40 can be configured to mount to either or both ends 14, 16 depending upon a particular purpose. For example, and as best shown in FIG. 1, the end 14 of the body 12 may include an annular recess 23 which is configured to receive a plurality of diametrically opposing, semi-resilient detents or locking pins 48 which protrude from an inner diameter 44 of the end cap 40 of FIG. 3A. As can be appreciated, the surgeon can easily grasp the outer periphery 42 of cap 40 and gently force the semi-resilient locking pins 48 towards body 12 until the pins 48 "snap" into recess 23. Preferably, a plurality of apertures 46 extend through end cap 40 thereby permitting direct growth or passage of bone or bone growth inducing substances through apertures 46.

Figure 3B:
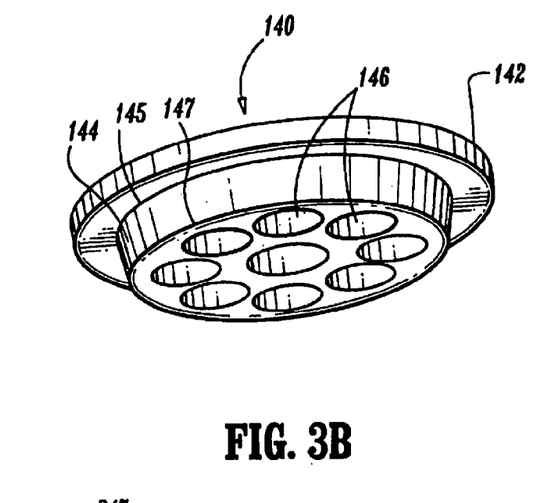
FIG. 3B is a bottom, perspective view of an alternate embodiment of the end cap having a diametrically tapered inner diameter.

FIG. 3B shows an alternate end cap 140 which includes an outer peripheral portion 142, an inner diameter 144 and a plurality of apertures 146 disposed therethrough. The inner diameter 144 generally tapers in an inward fashion, i.e., from an adjoining edge 145 which has a first diameter to a leading edge 147 which has a reduced diameter. The diameter of adjoining edge 145 is dimensioned slightly larger than the inner diameter 144 of elongated body 12 and the diameter of leading edge 147 is dimensioned slightly smaller than the inner diameter 144. As can be appreciated, this diametrically-tapered configuration of the inner diameter 144 allows the surgeon to quickly and easily wedge end cap 140 within the end 14 of the fusion cage 10 in a secure, friction-fit manner.

Figure 3C:
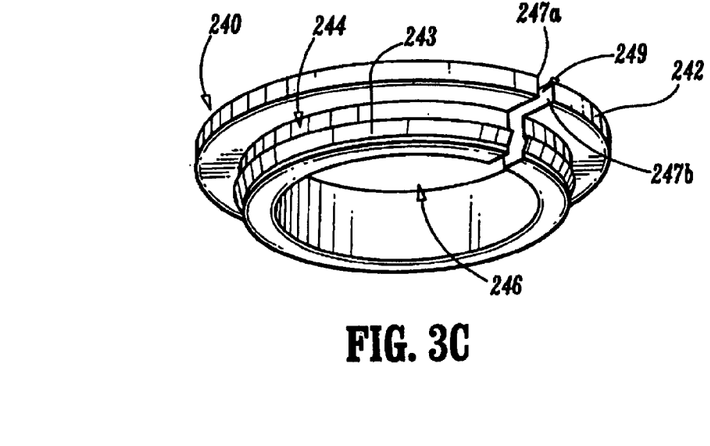
FIG. 3C is a bottom, perspective view of an alternate embodiment of the end cap having a C-shaped or split-ring configuration.

FIG. 3C shows another embodiment of an end cap 240 which includes an outer peripheral portion 242, an inner diameter 244 and a single aperture 246 disposed therethrough. The end cap 240 is generally C-shaped and includes two opposing ends 247a and 247b which define a slit 249 therebetween giving the end cap 240 an overall split-ring appearance.

The inner diameter 244 of end cap 240 also includes a flange 243 disposed about the outer periphery thereof. Flange 243 is dimensioned to "snap" into and seat within annular recess 23 of body 12 (See FIG. 1) after end cap 240 is inserted within body 12. Preferably, slit 249 is communicated through both the outer peripheral portion 242 and the inner diameter 244 such that the entire end cap 240 has some degree of radial resiliency. As can be appreciated, this enables the surgeon to quickly and easily mount the end cap 240 onto body 12 upon the application and subsequent release of inward, radial pressure. After the end cap 240 is mounted to body 12, bone or bone growth inducing substances can easily infiltrate cage 10, 100 through aperture 246 to promote fusion between the cage 10 and the vertebral bodies 202, 204.

Figure 6A:
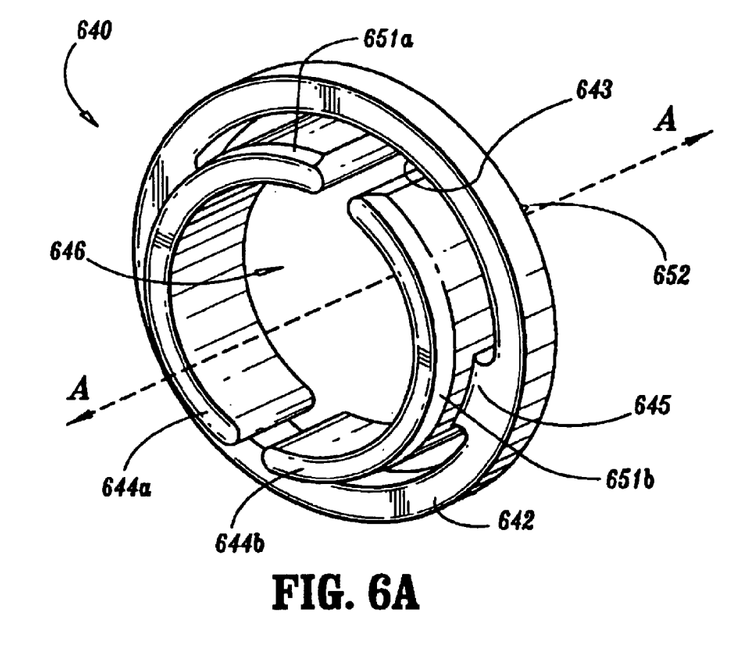
FIG. 6A is a rear, perspective view of an alternate embodiment of an end cap having a pair of retaining sleeves which secure the end cap to the fusion cage.
Figure 6B:
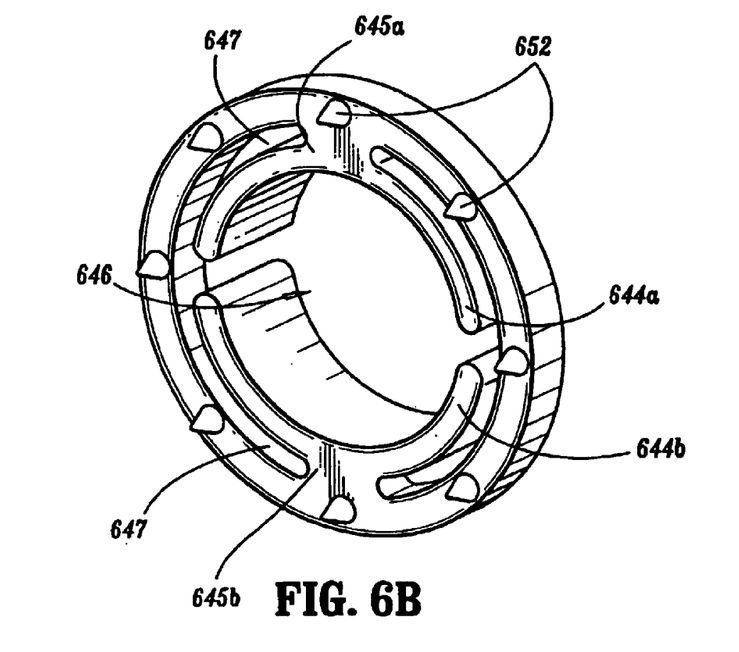
FIG. 6B is a front, perspective view of the embodiment of FIG. 6A.

FIGS. 6A and 6B show yet another embodiment of an end cap 640 according to the present disclosure which includes an outer portion 642 having an inner periphery 643 which defines a central aperture 646 therethrough. A pair of opposing, arcuately-shaped retaining sleeves 644a and 644b extend concentrically and distally along axis "A" with respect to inner periphery 643 and each include an outer rim-like flange 651a and 651b, respectively, at the distal end thereof. Preferably, arcuate sleeves 644a and 644b are semi-resilient and are dimensioned to mechanically engage the inner annular recess 23 of body 12. More particularly and upon insertion of end cap 640 into body 12, sleeves 644a and 644b radially compress inwardly towards axis "A" when end cap 640 is inserted within body 12 and outer flanges 651a and 651b "snap" into annular recess 23 to secure end cap 640 to cage 10.

As best seen in FIGS. 6A and 6B, the face of the end cap 640 also includes a plurality of spike-like detents 652 which are designed to anchor the cage 12 (once assembled with end cap 640) to the underside of the opposing vertebral bodies 202, 204. It is envisioned that these detents can be mounted or integrally incorporated with any one of the above-mentioned end cap configurations, e.g., 40, 140, 240, 340, 44, and 540.

Figure 4A:
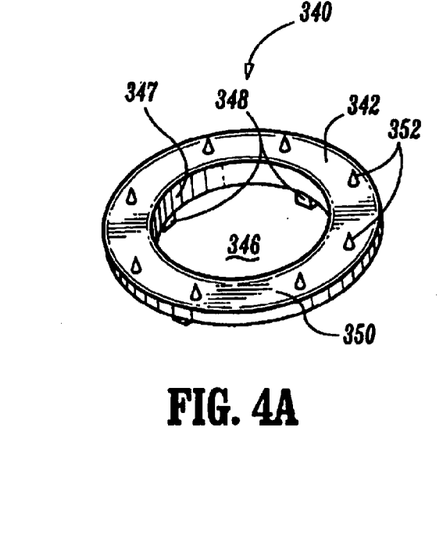
FIG. 4A is a top, perspective view of an alternate embodiment of an end cap having a central aperture located therethrough and a plurality of protrusions which project from the outer-facing surface thereof.

Moreover, various other configurations of detents are also envisioned. For example, FIG. 4A shows one arrangement of detents 352 which are integrally associated with a donut-like end cap 340. In this particular embodiment, the detents 352 are arranged in an array-like fashion about a centrally disposed aperture 346 defined through end cap 340. Preferably, detents 352 project from face 342 to engage the underside of the vertebral bodies 202, 204. It is envisioned that the detents 352 may project from face 342 at varying angles relative to the face 342 which may facilitate insertion and/or improve subsidence of the cage 10 into the vertebral bodies 202, 204.

Figure 4B:
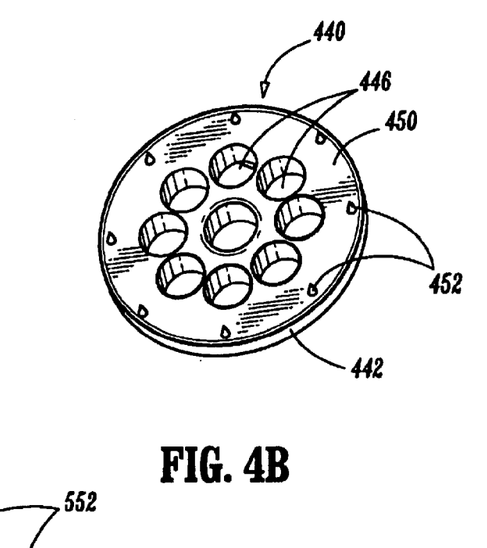
FIG. 4B is a top, perspective view of an alternate embodiment of an end cap having an array of centrally-located apertures located therethrough and a plurality of protrusions which project from the outer-facing surface thereof.

FIG. 4B shows another embodiment of an end cap 440 having a plurality of apertures 446 disposed through the face 450 thereof. Preferably, a plurality of spike-like detents 452 are arranged radially about the periphery of the face 450 proximate outer rim 442. As best illustrated in a comparison of FIGS. 4A and 4B, the detents 352, 452 may vary in size and dimension depending upon a particular purpose or to achieve a desired result.

Figure 4C:
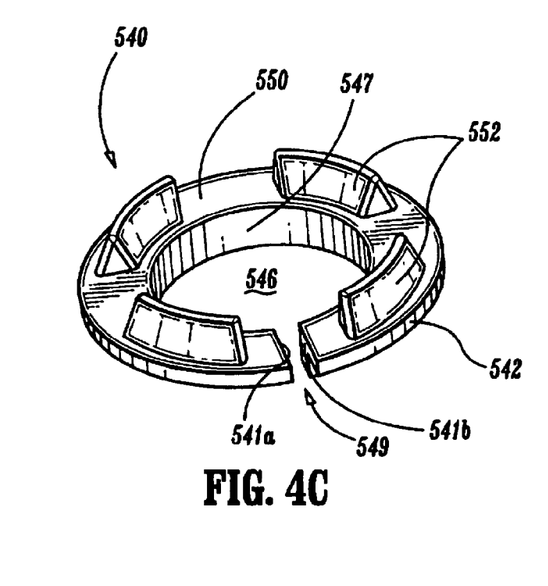
FIG. 4C is a top, perspective view of an alternate embodiment of an end cap having a central aperture located therethrough and a plurality of arcuately-shaped wedges which project from the outer-facing surface thereof.

FIG. 4C shows yet another embodiment of a C-Shaped end cap 540 having two opposing edges 541a and 541b which define a slit 549 therebetween. The end cap 540 also includes a face 550 having outer and inner peripheries 542 and 547, respectively. The inner periphery 547 defines a central aperture 546 therethrough which provides a passageway for the bone growth inducing substances which are used to promote fusion as mentioned above. A plurality of arcuately-shaped wedges 552 having a generally triangular cross section extend outwardly from the proximal face 550 and serve to anchor the cage 10 (once assembled with the end cap 540) to the underside of the vertebral bodies 202, 204. It is envisioned that the slit 549 allows the end cap 540 to contract radially inwardly to facilitate mounting the end cap to the cage 10 as described above with respect to FIG. 3C.

As can be appreciated, all of the above end cap embodiments snap into or mount to the cage 10 easily and readily without requiring screws or other retention devices.

The present disclosure also relates to a method of inserting a the fusion cage 10 into an intervertebral space "I" defined between vertebrae 202, 204. Initially, one lateral side of an intervertebral space "I" between the two vertebral bodies 202, 204 is accessed utilizing appropriate retractors (not shown) to expose the vertebral surface. Thereafter, a retractor is inserted within the intervertebral space "I" between vertebral bodies 202, 204 for distracting the vertebral bodies 202, 204 to a desired predetermined distance. A partial or full discectomy may be performed.

The modular fusion cage 10 is then assembled and sized to determine the appropriate number of ring segments, e.g., 13a, 13b, 13c and 13d, needed to fit in the intervertebral space "I" and maintain the adjacent vertebral bodies in the predetermined space during the fusion process. As can be appreciated, no internal rings are required because of the sharp edges or grooves 18 produced in the sizing device which allow subsidence into the vertebral bodies 202, 204. Moreover, the segmented design of the cage 10 eliminates the need for cutting tools and measuring guides.

The fusion cage 10 is then packed with bone growth inducing substances as in conventional in the art and one of the above-identified end caps is then mounted to the cage 10 in one of the above-identified manners. The cage 10 and end cap assembly is then mounted on an insertion instrument (not shown) and driven between the vertebral bodies 202, 204. As mentioned above, the spike-like detents 352, 452 or 552 promote subsidence into the vertebral bodies 202, 204.

Cage 10 is then released from the mounting instrument which is subsequently removed from the disc area. It is envisioned that a second end cap may be mounted to the distal end of cage 10 to retain the bone growth substances within cage 10.

Figure 5B:
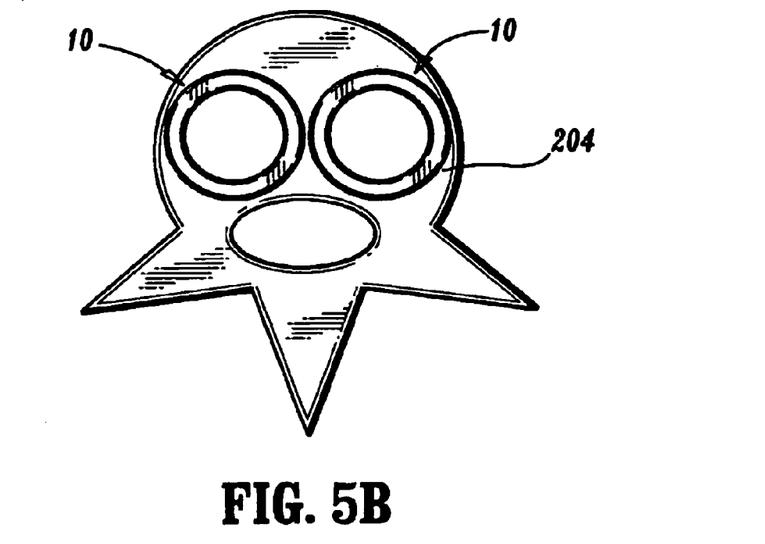
FIG. 5B is a schematic, top view showing a pair of fusion cages according to the present disclosure positioned within the intervertebral space for fusion of adjacent vertebrae.

A second lateral side of the intervertebral space "I" may be accessed and the above-described process is repeated to insert a second cage 10 in side-by-side relation as shown in FIG. 5B. Preferably, the cages 10, 10 are arranged such that the cages 10, 10 reside in adjacent side-by-side relation.

Once implanted, the fusion cages 10, 10 form struts across the intervertebral space "I" to maintain the vertebrae 202, 204 in appropriate spaced relation during the fusion process. Over a period of time, the vertebral tissue communicates through apertures 20 within cages 10, 10 to form a solid fusion.

From the foregoing and with reference to the various figure drawings, those skilled in the art will appreciate that certain modifications can also be made to the present disclosure without departing from the scope of the same. While the above description contains many specifics, these specifics should not be construed as limitations on the scope of the disclosure, but merely as exemplifications of preferred embodiments thereof. Those skilled in the art will envision other modifications within the scope and spirit of the claims appended hereto.

What is claimed is:

1. A fusion implant apparatus for facilitating fusion of bone structures, comprising:
   an implant member for positioning between opposed bone structures, the implant member having a segmentable portion having an outer wall defining an internal cavity for reception of bone growth inducing substances, the outer wall having at least one groove which extends substantially continuously about the outer wall forming a juncture between discrete ring-like segments on either side of the groove, wherein the outer wall of the implant member does not outwardly protrude between the adjacent ring-like segments, each ring-like segment including a plurality of apertures extending therethrough in communication with the internal cavity to permit fusion of the vertebral bone tissue, wherein none of the apertures and none of the at least one groove intersect each other; and
   the first end and/or the second end being dimensioned to engage an end cap.

2. The fusion implant apparatus of claim 1, wherein the groove acts as a cutting guide to determine the desired length of the fusion implant.

3. The fusion implant apparatus of claim 1, wherein the groove acts as a measurement guide to determine the desired length of the fusion implant.

4. The fusion implant apparatus of claim 1, wherein the outer wall includes a plurality of grooves that segment the body into discrete ring-like segments and do not intersect the apertures.

5. The fusion implant apparatus of claim 4, wherein the height of at least two of the ring-like segments are varied.

6. The fusion implant apparatus of claim 4, wherein the grooves are oriented parallel to each other.

7. The fusion implant apparatus of claim 1, further including an end cap which is mountable to the first or second end of the implant member.

8. The fusion implant apparatus of claim 4, wherein the end cap includes a face having at least one aperture disposed therethrough which communicates with the internal cavity to permit fusion of vertebral bone tissue.

9. The fusion implant apparatus of claim 4, wherein the face of the end cap includes a plurality of apertures disposed therethrough which are arranged in an array-like manner about the face.

10. The fusion implant apparatus of claim 7, wherein the end cap includes a face having a plurality of detents which extend outwardly therefrom, which serve to anchor the fusion apparatus to the bone structure.

11. The fusion implant apparatus of claim 10, wherein the detents are arranged radially about the face of the end cap.

12. The fusion implant apparatus of claim 10, wherein the detents are a spike-like configuration.

13. The fusion implant apparatus of claim 10, wherein the detents are arcuately-shaped and have a triangular cross section.

14. The fusion implant apparatus of claim 7, wherein the end cap includes at least one mechanical interface which engages the corresponding first or second end of the implant member.

15. The fusion implant apparatus of claim 14, wherein the mechanical interface of the end cap includes a plurality of locking pins which engage the first or second end of the implant member.

16. The fusion implant apparatus of claim 14, wherein the mechanical interface of the end cap includes a diametrically tapered inner diameter, which is dimensioned for friction-fit engagement within the first or second end of the implant member.

17. The fusion implant apparatus of claim 14, wherein the mechanical interface of the end cap is generally C-shaped and includes:
   two opposing ends which define a slit therebetween; and
   a flange which is dimensioned to engage an annular recess disposed within the first or second end of the implant member.

18. The fusion implant apparatus according to claim 14, wherein the mechanical interface of the end cap includes two opposing arcuately-shaped retaining sleeves which extend concentrically within an inner periphery of the end cap and are dimensioned to engage an annular recess within the first or second end of the implant member.

19. The fusion implant apparatus of claim 18, wherein the arcuately-shaped retaining sleeves include an outer rim which is dimensioned to engage the annular recess disposed within the first or second end of the implant member.

20. A method for fusing vertebrae, comprising the steps of;
   providing an implant member for positioning between opposed bone structures, the implant member having a first end and a second end dimensioned to engage an end cap, and a segmentable portion having an outer wall defining an internal cavity for reception of bone growth inducing substances, the outer wall having at least one groove which extends substantially continuously about the outer wall to define a plurality of discrete ring-like segments, each ring-like segment including a plurality of apertures extending therethrough in communication with the internal cavity to permit fusion of the vertebral bone tissue, wherein none of the apertures and none of the at least one groove intersect each other;
   accessing the vertebral space defined between adjacent vertebral bodies;
   determining the desired implant member length for insertion into the space between the adjacent vertebral bodies by using one of the grooves as a cutting and/or measurement guide;
   sizing the implant member; and
   advancing the implant member within the vertebral space between the adjacent vertebral bodies.

21. The method for fusing vertebrae of claim 20, further including packing the implant member with bone growth inducing substances.

22. The method of fusing vertebrae of claim 20, further including mounting an end cap to the first or second end of the implant member.

23. A fusion implant apparatus for facilitating fusion of bone structures, comprising:
   an implant member for positioning between opposed bone structures, the implant member having a first end and a second end, and a segmentable portion having an outer wall defining an internal cavity for reception of bone growth inducing substances, the outer wall having a plurality of grooves which extend substantially continuously about the outer wall to define a plurality of discrete ring-like segments, each ring-like segment including a plurality of apertures extending therethrough in communication with the internal cavity to permit fusion of the vertebral bone tissue, wherein none of the apertures intersect the grooves; and the first end and/or the second end being dimensioned to engage an end cap.

24. A fusion implant apparatus of claim 23, wherein the grooves act as cutting guides to determine the desired length of the fusion implant.

25. A fusion implant apparatus of claim 23, wherein the grooves act as measurement guides to determine the desired length of the fusion implant.

26. A fusion implant apparatus of claim 23, wherein the height of at least two of the ring-like segments are varied.

27. A fusion implant apparatus of claim 23, wherein the grooves are oriented parallel to each other.

28. A fusion implant apparatus of claim 23, further including an end cap which is mountable to the first or second end of the implant member.

29. A fusion implant apparatus of claim 28, wherein the end cap includes a phase having at least one aperture disposed therethrough which communicates with the internal cavity to permit fusion of the vertebral bone tissue.

* * * * *

UNITED STATES PATENT AND TRADEMARK OFFICE
CERTIFICATE OF CORRECTION

PATENT NO. : 6,899,734 B2
DATED : May 31, 2005
INVENTOR(S) : Michael Castro et al.

It is certified that error appears in the above-identified patent and that said Letters Patent is hereby corrected as shown below:

Column 7,
Lines 45 and 49, "claim 4" should read -- claim 7 --.

Signed and Sealed this

Sixth Day of September, 2005

JON W. DUDAS
*Director of the United States Patent and Trademark Office*